United States Patent [19]

Swanson

[11] 4,366,045

[45] * Dec. 28, 1982

[54] PROCESS FOR CONVERSION OF COAL TO GASEOUS HYDROCARBONS

[76] Inventor: Rollan Swanson, c/o Chemroll Enterprises, Inc., 100 Wall St., New York, N.Y. 10005

[ * ] Notice: The portion of the term of this patent subsequent to Dec. 28, 1999, has been disclaimed.

[21] Appl. No.: 268,190

[22] Filed: May 29, 1981

Related U.S. Application Data

[63] Continuation of Ser. No. 114,207, Jan. 22, 1980, abandoned, which is a continuation-in-part of Ser. No. 63,824, Aug. 6, 1979, abandoned.

[51] Int. Cl.$^3$ .......................... C10G 1/06; C10G 1/00; C10L 1/00; C10J 3/16
[52] U.S. Cl. ..................................... 208/10; 208/8 R; 208/8 LE; 208/108; 44/15 R; 48/202
[58] Field of Search .............. 208/8 R, 8 LE, 10, 108; 44/15 R; 48/202

[56] References Cited

U.S. PATENT DOCUMENTS

| | | |
|---|---|---|
| 1,300,816 | 4/1919 | Cobb . |
| 1,413,005 | 4/1922 | Cobb . |
| 1,904,586 | 4/1933 | Winkler et al. .................. 208/8 LE |
| 1,938,672 | 12/1933 | Ruthruff . |
| 1,974,724 | 9/1934 | Rosenstein . |
| 2,145,657 | 1/1939 | Ipatieff et al. |
| 2,950,245 | 8/1969 | Thomsen . |
| 3,112,257 | 11/1963 | Dauwes . |
| 3,185,641 | 5/1965 | Cowden . |
| 3,252,774 | 5/1966 | McMahon et al. |
| 3,354,081 | 11/1967 | Aldridge . |
| 3,368,875 | 2/1968 | Tulleners . |
| 3,382,168 | 5/1968 | Wood et al. . |
| 3,483,119 | 12/1969 | Ehrler . |
| 3,553,279 | 1/1971 | Dawa . |
| 3,565,792 | 2/1971 | Haskett . |
| 3,617,529 | 11/1971 | Thompson et al. . |
| 3,663,431 | 5/1972 | Warner . |
| 3,787,315 | 1/1974 | Bearden, Jr. et al. |
| 3,788,978 | 1/1974 | Bearden, Jr. et al. |
| 3,816,298 | 6/1974 | Aldridge . |
| 3,847,567 | 11/1974 | Kolina et al. .......................... 48/202 |
| 3,933,475 | 1/1976 | Swanson . |
| 3,957,503 | 5/1976 | Swanson . |
| 4,003,823 | 1/1977 | Baird, Jr. et al. |
| 4,007,109 | 2/1977 | Baird, Jr. et al. |
| 4,018,572 | 4/1977 | Swanson . |
| 4,057,422 | 11/1977 | Swanson . |
| 4,119,528 | 10/1978 | Baird, Jr. et al. .................... 208/108 |
| 4,147,611 | 4/1979 | Miasek et al. ........................ 208/108 |
| 4,147,612 | 4/1979 | Miasek et al. ........................ 208/108 |
| 4,155,717 | 5/1979 | Sun et al. ............................. 44/15 R |

FOREIGN PATENT DOCUMENTS

| | | |
|---|---|---|
| 161778 | 3/1955 | Australia . |
| 597489 | 5/1960 | Canada . |
| 590724 | 7/1947 | United Kingdom . |

OTHER PUBLICATIONS

Letoffe, et al., "Determination des Enthalpies de Formation Polysulfures de Potassium," *Journal de Chimie Physique*, 71, pp. 427-430, 1974.
Thomas, John S. and A. Rule, "The Polysulfides of the Alkali Metals", *Journal Chemical Soc.*, Part 3, pp. 1063+, 1917.
Biltz and Wilke-Dorfurt, *Z. Anorg. Chem.*, vol. 48, pp. 297-318, 1906 (See also *Ber.*, pp. 43-53, 1905).
van Krevelen et al., *Fuel*, 38, 256, 1959.
Mazumdar, B. K., et al., *Fuel*, 41, 121-128, 1962.
Hugot, *Ann. Chim. Phys.*, vol. 21, pp. 5-87 at 72, 1900.
Klemm, W., *Z. Anorg. Chem.*, band 241, pp. 281-304, 1939.
Bergstrom, F. W., *J. Amer. Chem. Soc.*, vol. 48, pp. 146-151 at 147, 1926.
Feher, F. and H. Berthold, *Z. Anorg. Chem.*, pp. 245-249 at 247, 1953.
Thomas and Rule, *J. Chem. Soc.*, 2819, 1914.
Eibeck, R. E., *Dissert. Abstract*, Ann Arbor, Mich., 21, p. 3254, 1961.
Renegade and Costeanu, *Compt. rend.*, L.156, pp. 791-793, 1913.
Renegade and Costeanu, *Academie des Sciences*, Seance due 30 Mar. 1914, pp. 946-946, (1914).
Sabbatier, *Ann. Chim. Phys.*, 22, pp. 5-97, 1881.
Marrony, *J. Chim. Phys.*, 56, 214-221, 1959.
Auroux, Mme. Aline, *C.R. Acad. Soc.* Paris, 274, pp. 1297-1300, Mar. 1972.

Kuster und Heberlein, "Beitrage zur Kenntnis der Polysulfide", *Z. Anorg. Chem.*, pp. 53–84, Nov. 1904.
Hamburger, Anna, "Uber die Festen Polyjodide der Alkalien, ihre Stabilitat und Existenzbedingungen bei 25°", *Z. Anorg. Chem.*, vol. 50, pp. 403–438, 1906.
"Alicyclicity of Coals: An Appraisal", *Fuel*, vol. XLI, pp. 105–111, 1962.
"Dehydrogenation of Coal by Iodine", *Fuel*, vol. 39, pp. 179–182, 1960.
"Dehydrogenation of Coal and Tar Formation", *Fuel*, vol. 37, pp. 112–119, 1959.
Foppl, H. et al., "Die Kristallstrukturen von —$Na_2S_2$ und $K_2S_2$, —$Na_2S_2$ und $Na_2Se_2$", *Z. Anorg. und Allgemeine Chem.*, Band 314, pp. 12–20, 1962.
Helms, Alfred et al., "Die Struktur der sogenannten", Alkalitetroxyde *Z. Anorg. und Allgemeine Chem.*, Band 241, pp. 96–106, 1939.
Goubeau, Josef et al., "Das System Kaliumsulfat–Kaliumsulfid", *Z. Anorg. und Allgemeine Chem.*, Band 236, pp. 45–56, 1938.
Klemm, Wilhelm, "Das Magnetische Verhalten der Kaliumpolyoxyde und -Polysulfide", *Z. Anorg. und Allgemeine Chem.*, Band 225, pp. 273–280, 1935.
Mazumdar, B. K., "Alicyclicity and Smoke Emission of Coal", *Nature*, vol. 183, p. 1613, Apr. 4, 1959.
Mazumdar, B. K., "Dehydrogenation Studies on Coal", *Journal of Scientific & Industrial Research* (India), vol. 17, pp. 509–511, 1958.
Pearson, Thomas Gibson et al., "The Polysulfides of the Alkali Metals, Part III, Potassium", *J. Chem. Soc.*, Part I, pp. 1304–1314, 1931.
Thomas, John Smeath et al., "The Polysulphides of the Alkali Metals, Part V, The Monosulphide and Disulphide of Lithium", *J. Chem. Soc.*, vol. 125, Part II, pp. 2207–2219, 1924.
Thomas, John Smeath et al., "The Polysulphides of the Alkali Metals, Part IV, The Polysulphides of Ammonium" *J. Chem. Soc.*, vol. 123, Part II, pp. 1726–1738, 1923.
Thomas J. Smeath et al., "The Sulphides of Ammonium", *J. Chem. Soc.*, vol. 123, pp. 1181–1189, 1923.
Pollitzer, F., "Uber das Gleichgewicht der Reaktion $H_2S + 2J = 2HJ + S$ und die Dissoziation des Schwefelwasserstoffs", *Z. Anorg. Chem.*, vol. 64, pp. 121–148, 1909.

*Primary Examiner*—Delbert E. Gantz
*Assistant Examiner*—William G. Wright
*Attorney, Agent, or Firm*—Fred A. Keire

[57] ABSTRACT

A process for converting coals to principally hydrocarbon gases, by intimately contacting coals such as lignite coal with a reagent, e.g., alkali metal polysulfides or alkali metal hydrosulfide, in the presence of steam, or a combination of steam and hydrogen, at temperatures between 65° C. to 450° C. Liquid and gaseous hydrocarbons of preselected compositions may be produced; as it is well known these are useful as fuel, or as chemical starting materials, e.g., for upgrading fuel or making industrial chemicals.

34 Claims, 1 Drawing Figure

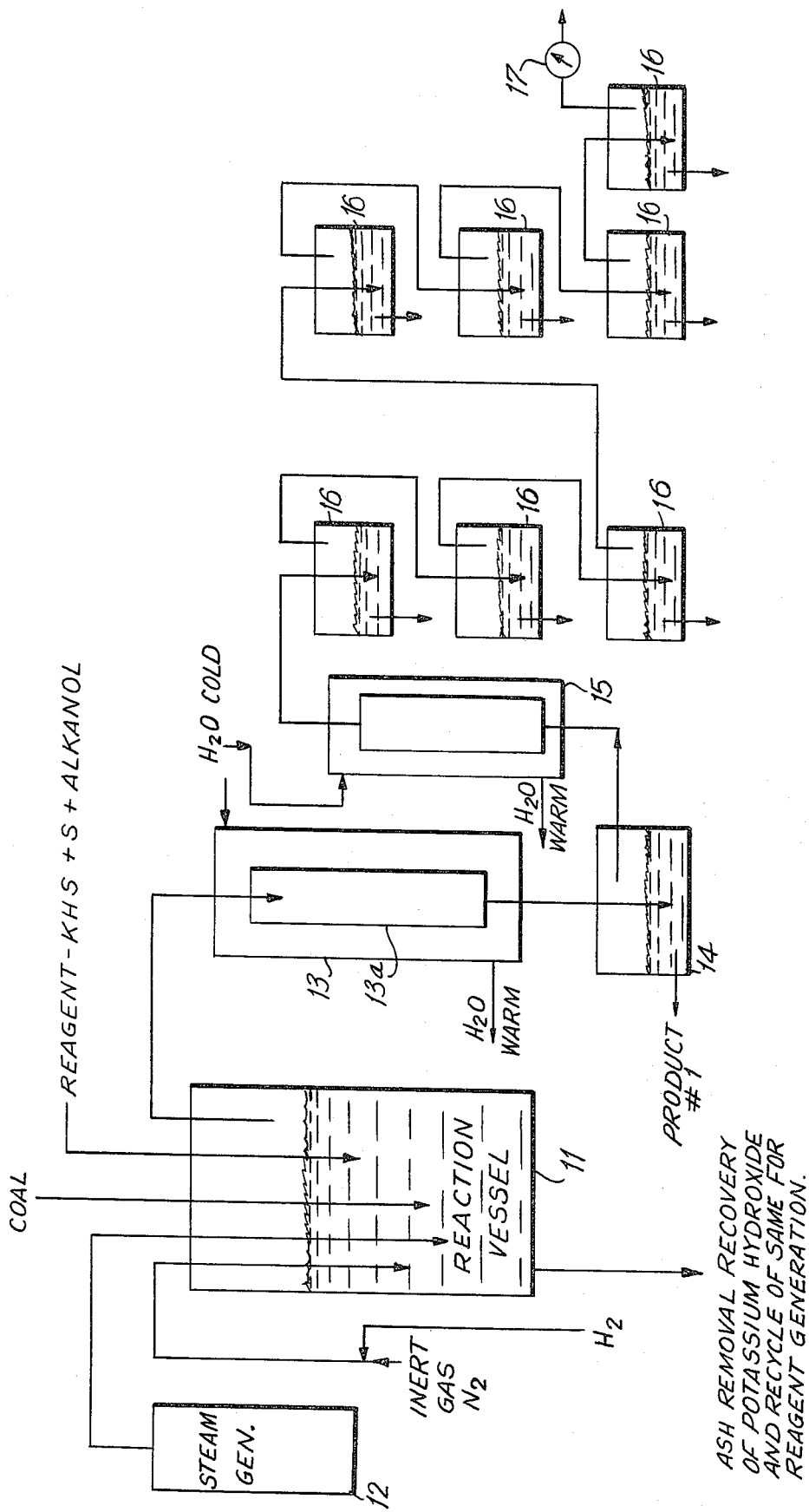

PROCESS FOR CONVERSION OF COAL TO GASEOUS HYDROCARBONS

This is a continuation, of application Ser. No. 114,207, filed 1/22/80 now abandoned which in turn is a continuation-in-part of application Ser. No. 63,824 filed Aug. 6, 1979 now abandoned.

In my previous application I disclose a method for preparing an alkali metal reagent based on the reactions of this reagent with oxygen, nitrogen and sulfur in coal. The disclosure of the above application is incorporated by reference herein.

This further invention relates to conversion of coal to various useful component parts thereof, principally gaseous component parts and conversion of these gaseous components into other distillates; more particularly, this invention relates to the conversion of coal to desired conversion products thereof such as hydrocarbons in liquid or gaseous form by reacting coal with a particular reagent therefor, in presence of water, steam and/or hydrogen, at a low to moderate temperature and at atmospheric pressure.

Still further, this invention relates to conversion of coal to various preselected component cuts thereof, principally gaseous component parts, by means of a specific reagent, whereby coal, in the presence of this reagent water, steam, and /or hydrogen, is converted into useful breakdown materials thereof. These breakdown materials are principally gaseous hydrocarbons which may be recycled to obtain liquid distillates. Ultimately, at the high temperatures, coal in presence of the reagent and steam causes production of some hydrogen. The residue of the coal comprises ash and reagent from which the reagent may be recovered and reused.

BACKGROUND OF THE INVENTION

It has become increasingly evident that liquid and gaseous hydrocarbon sources such as petroleum and natural gas are being depleted at such rapid rate that an intensive effort is needed to meet anticipated future needs for obtaining substitute energy, feedstock, or chemical starting materials. One of the most readily available sources of hydrocarbon materials is coal. Heretofore, there has been no ready means, without extensive capital investment on economically justifiable basis, to produce hydrocarbons from coal. Although various processes are known for conversion of coal at high temperatures, such as high temperature i.e. above 600° C., high pressure e.g. above 25 atmospheres coal gasification, there has been no readily available lower-temperature, low-pressure process which would readily convert coal into its component hydrocarbons.

PRIOR ART

In considering the present invention, applicant is aware of the following patents: U.S. Pat. Nos. 3,926,775, 3,933,475, 3,944,480, 3,960,513, 3,957,503, 4,018,572, 4,030,893, 4,057,422, and 4,078,917.

GENERAL DESCRIPTION OF THE INVENTION

It has now been found that when coal is treated with a particular reagent, it can be converted in the presence of this reagent and in the presence of steam to various hydrocarbon fractions principally gaseous hydrocarbon fractions of one to five carbon atoms ($C_1$ to $C_5$), e.g., methane, ethane, ethene, etc.

Further, it has been found that when this conversion is being carried out at different temperatures, i.e., using steam and coal at set steps, at elevated temperatures, the proportion of the various hydrocarbons obtained from the same coal can be changed. At lower temperatures volatile liquid hydrocarbons will be produced. At higher temperatures, principally gaseous hydrocarbons will be produced.

Still further, it has been found that various coals, that is, lignites of various compositions and sub-bituminous coals show different distillation points although the production of the liquid and gaseous hydrocarbons will still take place. Higher value (rank) coals give more liquid hydrocarbon distillate than do lower value coals while other process or reagent modifications allow the obtention of more liquid distillates.

In general terms, it is believed that when the alcoholic solution of KHS by itself (or with sulfur) is being added to the coal, a reaction takes place as follows: $KHS + S_2 \rightarrow \frac{1}{2}H_2S + \frac{1}{2}K_2S_5$. From the above it follows that KHS may be used without sulfur addition. However, sulfur tends to stabilize KHS as a less hydrolyzed polysulfide. There is some breakdown of KHS to $K_2S$ in the presence of water. This breakdown is partial. Hence, in hydrogenating coal, both KHS and $K_2S$ should be present in the reaction. When sulfur is added less hydrolyzed and therefore a more water-stable polysulfide is provided.

Although the above reaction is shown for KHS, NaHS will also work, but appears to work best without elemental sulfur addition.

It is also possible to use KHS or NaHS in dry state, i.e., without alcohol addition. NaHS is obtainable as an industrial bulk commodity, generally in a flake form with about 30% by weight of water in the bulk form.

When the $K_2S$ and various polysulfide species thereof, reacts with coal, it preferentially attacks the oxygen, sulfur and nitrogen present in coal in a bound form to withdraw these components of coal. As these components are forming in the presence of steam or water, the bond scission of the various coal constituent parts and abstraction of oxygen, nitrogen and sulfur, allow the introduction of hydrogen and thus the formation of hydroaromatic, aromatic and shorter chain aliphatic compounds.

It has been found that oxygen must be present in the coal. For this purpose, low quality coals, such as lignites, are very suitable. As the quality of the coal increases, such as in sub-bituminous coal, the amount of oxygen in these coals decreases and consequently, the possiblity for gaseous conversion decreases thereby, and/or more liquid phase components are produced. It has also been found that even sub-lignite coal and peat can be converted according to this method into various hydrocarbon components.

In order to illustrate the present invention, a drawing has been enclosed herewith wherein:

The FIGURE shows the schematic reaction train of the coal conversion and component recovery.

Turning now to the Figure, the reaction vessel 11 is typically a retort or a similar device in which coal in a finely ground stage is being fed. Typically, particle size of coal is up to ¼ inch for lignite and can be more, as the reaction is size independent. For sub-bituminous coal the particle size can be up to ¼ inch but is preferably about 1/32 of an inch. After the system has been first purged of any oxygen by introducing inert gas such as hydrogen or nitrogen, etc., $K_2S$ or KHS (or equivalent)

in alcohol reagent is introduced therein. The system is then closed and the temperature is elevated to 65° C. at which temperature the alkanol from the reagent is distilled. As the inert gas, i.e., nitrogen, or hydrogen, provide the agitation, the continuous expulsion of water continues along with the expulsion of the alkanol. Typically, the alkanol is methanol or ethanol, although higher alcohols may be used such as alkanols up to 4 carbon atoms.

Once the desired operating temperature is reached (after alkanol distillation—if used in the process) and steam at an appropriate temperature is being introduced into the system, the inert gas such as nitrogen, first used to purge the system of oxygen, may no longer be needed. The steam vessel 12 is provided with means for heating water in the same or auxiliary heating may be supplied such as by heating the line from the steam generator 12 to reaction vessel 11.

An appropriate means for monitoring or controlling the reaction in the reaction vessel may also be provided such as heating or cooling coils, temperature gauges, heat control elements, stirring devices, etc. The reaction vessel may also be externally heated.

The reaction products from the reaction vessel are introduced into the condenser 13, which may be of a refluxing type with the in and out water temperature adjusted to condense the heavy fraction first coming over from the coal. The heavy fraction may condense on the walls of the condenser device 13a and then descend downwardly until received in the bottom collector 14 from which these liquid products may be removed, recovered and analyzed from time to time.

From the bottom collector 14, the gaseous effluent is then sent on to a second condenser 15 where the gaseous products are further cooled and introduced into the scrubbers 16. In these scrubbers 16 appropriate scrubbing liquids are kept so as to collect the desired product fraction in each of the scrubber liquids. On an industrial scale, separation in a distillation column may be more practical.

The nonsolubilized but scrubbed component, in its gaseous form, in turn, is introduced into the next scrubber, from which further components are separated (as will be further explained herein). Although seven scrubbing stations have been shown, the number depends on the gaseous fractions sought to be recovered. Hence, the number of the scrubbing sections may be increased or decreased. The final gaseous fraction is metered by meter 17 and may be collected and treated such as by further scrubbing and purification, i.e., distillation, or it may be used directly.

As it is well understood, inasmuch as the gaseous fraction from the gasification of coals is a fairly narrow fraction consisting in the major part of gaseous fractions having from 1 to 6 carbon atoms or near liquids thereof, fractionation may also be employed for recovery of the various reaction products. Typical fractionation means are such as a distillation tower and molecular sieve separation means. These separation and distillation means are well known to those skilled in the art and need not be illustrated.

For purposes of this invention, however, an embodiment is shown which allows the separation of various fractions based on the solubilities of the hydrocarbons having from 1 to 6 carbon atoms.

This process may be carried out continuously. Thus, the separation function for the various reactants (such as the alcohol based reagent) may be effected in such a manner that the system may operate continuously with continuous introduction of reagents, coal, and steam and continuous removal of product. Under those conditions, inert gas purging may not be necessary. From each of the scrubbers 16 the dissolved component may be separated by conventional means and the liquid used therein separated therefrom.

Turning now to the solubilities which have been given herein, typically, these are for the indicated gas at normal room temperature defined as 72° F. Inasmuch as the scrubbing process can be operated at room temperature and at near atmospheric pressure, the solubilities are intended to be for those conditions. It is noted that higher pressures may also be used such as in a distillation train so as to avoid any excessively low temperatures. Again, when the pressure conditions are changed, the recovery which may be effected at the changing pressures is well understood by those skilled in the distillation art.

Based on the well known solubility factors, such as available from reference handbooks, these are listed for the hydrocarbons recovered from the system. Solubilities of $C_1$-$C_6$ hydrocarbons are as follows:

Ethene is soluble in ether, slightly soluble in alcohol, acetone and benzene and insoluble in water. Ethane is soluble in benzene, slightly soluble in alcohol and acetone and insoluble in water. Propane is soluble in water and in alcohol, very soluble in ether and benzene and slightly soluble in acetone. It is also very soluble in chloroform. Propene is very soluble in water, in alcohol and in acetic acid. Butane is very soluble in alcohol and ether and chloroform and is soluble in water. Butene (1- & 2-) is very soluble in alcohol and ether, is soluble in benzene and insoluble in water. 1-,2-, and trans-pentene is miscible in alcohol and ether, very soluble in dilute sulfuric acid, and soluble in benzene but insoluble in water. Pentane is miscible in alcohol, ether, acetone, benzene, chloroform and heptane slightly soluble in water. Hexane is soluble in ether and chloroform and very soluble in alcohol and insoluble in water. Hexene (1-,2-, trans, 3-) are soluble in alcohol, ether, benzene, chloroform, pet. ethers, and insoluble in water. Methane is soluble in water, alcohol, ether, benzene, methanol and toluene and slightly soluble in acetone.

The reagent such as the potassium hydrosulfide and sodium hydrosulfide or a polysulfide thereof is reconstituted such as in one of the reaction vessels when the scrubbing liquid therein is alkanolic KOH, or NaOH to form either the appropriate sulfide or hydrosulfide depending on the amount of $H_2S$ to react with the hydroxide. Typically, at those conditions the reagent will precipitate as a white precipitant, e.g., of the formula $K_2S$ (hydrate) or $Na_2S$ (hydrate). In ethanol or higher alkanols the only slightly soluble alkali metal sulfide can be removed from the system by merely withdrawing the precipitate from the scrubber.

The ash remaining in the reaction vessel 11 is appropriately removed therefrom and worked up such as by dissolving the solubles therein and extracting, e.g., potassium therefrom based on the differential solubility of calcium hydroxide and potassium hydroxide, that is, extracting potassium with calcium hydroxide precipitating calcium sulfate and removing potassium hydroxide. Sodium hydroxide is present in the ash in lesser quantities and may be removed in the same or different manner, as it is well known in the art. As sodium is present in coal in considerably smaller proportions than potassium, sodium may have to be augmented during the continuous process if sodium based reagent is used. There is sufficient amount of potassium present in coal. As it is evident from the above, at lower temperatures, for lignite such as given in the example (to follow) the reaction provides a hydrocarbon fraction which is in the $C_3$–$C_6$ hydrocarbon range with the fraction having an average of $C_4$ predominating. This fraction is typically recovered up to about 120° C. At 220° C., the methane through butane fraction is being produced including the corresponding double bond unsaturates. At 360° to 450° C., typically ethene and possibly some hydrogen is being produced. In order to assure that no hydrogen sulfide is being expelled, the product stream is scrubbed in an alkali metal e.g. potassium as sodium hydroxide alkanolic solution at saturated conditions. The hydrogen sulfide reacts wth the hydroxide to regenerate the reagent i.e. $K_2S$ and $Na_2S$ and in presence of water regenerates KHS and NaHS. In the thus scrubbed gas stream, hydrogen sulfide is present in a very small amount e.g. less than 0.01%, by volume.

The above illustration of the process as well as the invention herein is described by reference to the examples which are not intended as a limitation of the invention, but rather as an illustration of an embodiment thereof.

EXAMPLE 1

Fifty milliliters of a methanol solution of potassium hydrosulfide, containing 0.37 grams of potassium hydrosulfide/ml. were used as the base reagent. 71 grams of a lignite were used having a "dry ashless" content of 66% carbon, 3.97% hydrogen, 18.2% oxygen, and 0.9% nitrogen, by weight, plus a small amount of volatiles. The raw lignite contained 33% water and 9% dry ash. (The "as received" wet analysis was 6% ash). The organic sulfur content of this lignite was 0.69% and the pyritic sulfur content was unknown.

The run was made with lignite which has been dried for 2 hours at 135° C. and with lignite which had not been dried. The principal difference between the dry and wet lignite was a production of very light hydrocarbon gases from the wet lignite at temperatures below the boiling point of water during the period that the temperature was being elevated. Water from the lignite provided the hydrogen for this production of hydrocarbon distillate. In other respects, the reaction proceeds the same.

Elemental sulfur was added to the lignite. It may also be added to the alcoholic KHS solution. The total amount of sulfur present was 8.25 grams, which included the organic sulfur content of the lignite.

The apparatus consists of a container and a conduit for hydrogen or nitrogen as the flushing inert gases (see Figure herein). These inert gases may be fed directly or are fed through a steam generator via a steam line into the reaction vessel 11. The steam line is heated to 140° C. and enters the reaction vessel near the bottom of the vessel heated at that temperature.

Means for measuring temperature are also provided. Typically, the steam line enters through the center opening for the flask. Initially, nitrogen or hydrogen provides the agitation while the methanol of the reagent solution is being distilled. Agitation may be effected by different means as well, such as stirring. The presence of water in the raw lignite produces a methanol (or ethanol) soluble hydrocarbon gas during this distillation.

This liquid hydrocarbon production is minimized when dry lignite is used. The reaction vessel 11 may be of a suitable form, but as used in this experiment, it is a round bottom flask, with appropriate introduction ports at the top thereof.

Another introduction port is for the addition (and removal) of lignite. The reagent is introduced through an appropriate opening which is closed during the run.

A still further port leads to a vertical water cooled condenser which empties into a round condensation flask 14 having an outlet port therefor and a port, at the bottom, for removal of distillates.

Residual gases pass from the condensation flask (vessel) 14 into a second water-cooled condenser 15, conveniently above the same condensation flask 14.

The gases from the condensation flask, i.e., remaining gases, are then passed through a series of scrubbers. The scrubbers consist of at least the following: (a) a water wash, (b) an ethanol (methanol) wash, (c) a one mole solution of KOH in 135 ml of methanol, (d) a benzene wash, (e) a one mole solution of KOH in two moles of water, (f) sulfuric acid wash of about 24% solution of a 98% $H_2SO_4$. As a back-fire preventer, an empty scrubber may be used.

The remaining gases thereafter pass through a conduit and are suitably collected by suitable collection means. A chromatograph tube may be inserted before the gas test meter 17 (placed between the scrubbers and the collection means) so that gas samples can be analyzed. A chromatograph tube may also be inserted where desired, in the recovery train and the gases or distillates analyzed.

A gas meter, on this line, calibrated in fractions of a cubic foot, gives a cumulative total of cubic feet of hydrocarbon gas recovered.

In conducting the process, the lignite (and the sulfur it contains) is placed in the reaction vessel and heated to 35°–50° C. 50 ml of reagent are added after flushing the system with hydrogen or nitrogen to expel atmospheric oxygen. The system is closed and the temperature elevated to 65° C., at which temperature the methanol component of the reagent is distilled. As mentioned before, the introduced hydrogen or nitrogen may provide sufficient agitation of the reagent-lignite mixture. The reagent also contains water both as impurities in the ingredients used to make the reagent and additional water is formed as the reagent is formed. The water present in the reagent and coal is distilled off at temperatures up to 135° C.

The distillate produced during the distillation of the methanol (or ethanol) will contain methanol or ethanol soluble hydrocarbon components including gases. Water is distilled from the reaction mass, after most of the methanol has been removed, it is mostly clear. This water may contain a small quantity of amber colored liquid hydrocarbons (which increases with coal rank). At a temperature from 135°–190° C., but typically at 135°–170° C., a small liquid hydrocarbon fraction will be produced from the reaction mass; again this amount increases with the rank of coal. This liquid hydrocarbon condenses within the water cooled condenser 13, on the walls 13a of the condenser as a solid or semi-solid.

After the water-methanol mixture has been distilled from the reactant mass, optionally, the introduced hydrogen or nitrogen can be turned off. At that point, i.e., at about 170°–190° C. steam alone is used to agitate the mix or a suitable stirrer may be used. Steam is not introduced into the reaction vessel until the methanol-water mixture has been distilled because the water-methanol mixture will hold the temperature at a specific temperature range during this distillation.

After the introduction of the steam or the steam and continuing hydrogen introduction, various lignites and subbituminous coals, based on the inherent makeup of these, display different distillation points in the production of sizable amounts of gaseous hydrocarbon.

It is suggested to discontinue the introduction of hydrogen, when steam is injected into the reaction vessel, because an accurate test meter reading of the quantity (volume) of gas emitted from the apparatus cannot be made when hydrogen is being introduced into the apparatus. However, appropriate means such as a second test meter on the hydrogen tank would give an indication of the amount of hydrogen passing into the system and this could be subtracted from the total reading of the final test meter 17. It should be mentioned that some of the hydrogen is utilized to hydrogenate the coals and that quantity of hydrogen cannot be measured by these means.

Generally, for low rank coal a sustained production of hydrocarbon gases begins at the boiling point of the methanol or ethanol and continues to increase as the reaction mass is heated to approximately 280° C. For higher rank coal, at these low temperatures, i.e., up to about 280° C. little if any gas production takes place. These gases are mostly taken up in the scrubber system and very low reading is given on the gas meter 17.

If the scrubber system is eliminated (and the initial hydrogen sulfide production, from the reaction between the alkanolic reagent and the elemental and organic sulfur—the last in the coal—is separately vented or measured or scrubbed with a suitable aqueous reagent), the gas quantity can be measured.

As previously mentioned, depending on the particular coal, the initial quantity of gas is low, e.g., from lignite at temperatures below 280° C. about 0.025 to 0.05 cu. ft./50 grams of gas is obtained from the wet coal.

Methane is generally given off first and it has the greatest solubility in all of the scrubber system liquids as compared to each of the other recovered hydrocarbons. Pentane, hexane, hexene and pentene also have a considerable solubility in the scrubber liquids used in the system, except in water. Hexanes and hexanes condense in the water cooled condenser and are only gasified further as influenced by the partial pressure of the other lighter gases passing over the liquid. A component of the gas recovered and entering meter 17 is ethene. Ethene has a limited solubility in the kerosene and little solubility in the water and alcohol in the various scrubbing stations 16. Ethene has a characteristic smell of unsaturated hydrocarbon while the saturated hydrocarbon gases are odorless. Solubility of unsaturated hydrocarbon gases in sulfuric acid can be used to separate the saturated from the unsaturated hydrocarbons.

When the temperature reaches 335° C., the initial 100 grams of wet lignite or sub-bituminous coal provide a more rapid gas production in the $C_1$ to $C_5$ carbon atom range. The gas production increases substantially when 360° C. is reached and when the final temperature is between 380° C. and 450° C. a very rapid gas production is encountered with some hydrogen being produced. At a temperature of 360° to 380° C. carbonyl sulfide is also produced and in sub-bituminous coal e.g. 4.7% by weight of the total hydrocarbon gas may be carbonyl sulfide.

At the higher temperature, gases pass the scrubbers and are registered on the flow meter. For example, from 100 grams of wet sub-bitumminous coal, after subtracting for hydrogen sulfide, generally up to 1.4 cubic feet or gas from 47 grams of carbon (on dry basis) present in the sub-bituminous coal can be obtained at the higher temperatures.

A standard temperature and pressure, about 3.7 moles of gas containing 47 grams of carbon would indicate an average carbon content of 2.25 for a product. Again, it should be noted that the products produced at different temperature levels consist of different breakdown fractions.

Gas chromatographic analysis on Example 1 run, gives a strong indication of two hydrogen atoms to each carbon atom in the gases. The initial lignite contained one hydrogen atom for every 1.38 carbon atoms, or, for a direct comparision, 0.725 hydrogen atoms to each carbon atom. Gas chromatographic analysis did not indicate any substantial oxygen present and showed that the collected gases were almost entirely hydrocarbon. The hydrocarbon gases containing from 1 to 6 carbons in that fraction are either gases or very volatile liquids.

The scrubbers do remove carbon dioxide as potassium carbonate as a precipitate in the KOH-ethanol or -methanol solution. Generally, a solution of one mole KOH in two moles of water is used, and the alkanol can be added to this aqueous solution of the alkali metal hydroxide.

EXAMPLE 2

25 grams of industrial grade sodium hydrosulfide flakes were mixed with 100 grams of Maverick sub-bituminous coal. Industrial grade NaHS is in flake form and of varying analysis and this particular sample contained approximately 30% water. These flakes were placed on top of the coal in the reaction vessel. The coal analysis was:

moisture 3.3%; ash 12.9%; sulfur 0.69%; carbon 70.2%; hydrogen 4.4%; nitrogen 1.13%; and oxygen 6.16% by weight.

The heating value for the coal is 12,656 BTU/lb.

The mixture was heated to 280° C. in a reaction vessel. Steam was injected (140° C. steam) at the bottom of the reaction vessel to provide agitation and supply hydrogen for the hydrogenation of the coal. Steam was injected after a temperature of 175° C. was reached. It is believed that the hydrosulfide was decomposed at least partially to the sulfide during this heating as a result of the water content in the reagent and coal.

Below 175° C., a few clear drops of hydrocarbon distilled with the initially expelled water. The reagent bubbles up at 175° C. apparently due to the formation of a lower hydrate of sodium sulfide with the subsequent release of water.

At 280° C. the hydrogen gas given off was produced on a continuing basis and a flame could be sustained at the end of the system in the glass tube. The gases were water washed prior to burning. At 350° C. the run was terminated with about half the coal reacted.

The liquid distillate, cooled and condensed in a water cooled condenser was 15 ml and gave an analysis of 9.8% hydrogen, 87% carbon and 0.67% sulfur and 0.07% nitrogen. By chromatographic analysis, the gases were principally ethene. Approximately 0.8 cu. ft. of gas was produced.

Without being bound to any particular theory, in the practice of this invention, it is believed that oxygen, sulfur and nitrogen are removed from coal by a series of complex reactions made possible by sulfur compounds of potassium or equivalently by the other alkali metal sulfur compounds, as will be explained below. The reactions, via the water and hydrogen sulfide molecules, provides hydrogen to react with coal at the point where coal is being deoxygenated, desulfurized or denitrogenated. Hence, for practice of this invention, it is necessary that oxygen be present in coal but the benefit is also gained when sulfur and nitrogen is present in coal in a form such as an organic sulfur or organic nitrogen species. Moreover, higher rank coal, such as bituminous coal, may not be readily be converted to gaseous hydrocarbons although, as explained below, it still may be done when the reaction scheme is appropriately modified.

It has been found that coal with a carbon content below about 70% was almost entirely gasified with no more than 5% being a solid and/or liquid distillate. A coal with about 75% carbon content gave a 10% liquid distillate; the rest was gas. A coal with 82.5% carbon gave 33% liquid distillate; the rest was gas. An anthracite coal of 92% carbon content gave little gas and only about 2% liquid-solid distillate. When sodium is used, instead of potassium, about the same amount of liquid distillates are produced, but less gas.

For this reason, the present invention is concerned preferably with lignite and sub-bituminous coal gasification. Further, this invention is applicable to sub-lignite and even peat gasification, but economic factors do not render the process as advantageous, due to the lower carbon content in these source materials per equivalent weight.

Although rubidium is equally active, for practical reasons, potassium is the preferred hydrosulfide. Sodium is also useful as sodium hydrosulfide and polysulfides do undergo the necessary reactions. Cesium, rubidium, potassium and sodium, hydrosulfides and polysulfides are useful but cesium and rubidium are not cost advantageous. Lithium may also be used, but is less effective than sodium. A mixture of rubidium, potassium and sodium sulfides (generic), may be used with greater effectiveness than any of the individual (generic) sulfides. The term "generic" is intended to mean the series of sulfides beginning with hydrosulfides to polysulfides. The preferred ratio is 14% rubidium, 26% potassium and 60% sodium sulfides (generic) by weight of the elemental metal. The ratio ranges for the preceding mixture are 1:1.5–2.5:3.5–4.5, respectively.

The amount of potassium hydrosulfide to coal is from 5 to 30 grams per 100 grams of coal with about 10 to 25 grams being normally employed. Typically, about 18 grams of potassium hydrosulfide per 100 grams of coal is used. However, as will be further explained herein, this reagent is reconstituted. If potassium in coal ash is converted to hydrosulfide no loss of potassium hydrosulfide in experienced; and the reagent balance for the reaction, on batch or continuous basis, is very favorable.

In general, it is emphasized that sufficient amounts of sulfur, sulfide, hydrosulfide or polysulfide should be present to take up the sulfur expelled from coal by oxygen during deoxygenation thereby preventing the expelled sulfur from dehydrogenating the coal at a temperature above 175° C. Also, the integrity of the various reagent species must be preserved above 325° C. since a temperature increase above this level will cause a slow de-hydrogenation of coal by alkali metal hydroxide melt. As sulfur causes the formation of polysulfides and the alkali polysulfide is less hydrolyzed with increasing sulfur content thereof, the decomposition by steam (or other water) of the hydrolysis product, i.e. the hydrosulfide is thereby prevented.

Consequently, the selection of the necessary amount of reagent is fairly certain for each type of coal and can be readily established for that coal based on the above broad ranges for the reactants and the amounts of sulfur present in coal.

In calculating sulfur in coal, only organic sulfur, i.e., sulfur bound to carbon, is taken into consideration. Nitrogen in coal is converted to ammonia and, for a large scale operation, may be recovered as a valuable by-product.

Steam as shown above is employed at a temperature at which the reaction is sought to be conducted, i.e., depending on the type of coal and the decomposition levels of coal as well as the desired product. Steam also provides a source of hydrogen apparently as $H^+$ (apparently not from $OH^-$). Appropriate steam generation at the selected temperature may be in the generator 12 shown in the Figure. As a suitable amount, sufficient steam is used, e.g., to provide hydrogen for hydrogenation of coal having a hydrocarbon end product from one to two carbon atoms. If less hydrogenation is sought, less steam is used.

As the amount of sulfur content of the reagent is increased, i.e., from sulfur in coal and added elemental sulfur, the reaction temperature is lowered. For example, a reaction temperature of 380° C. is lowered to 310° C., when, as an illustration, the sulfur balance is representative of a theoretical compound $K_2S_3$ produced and maintained during reaction conditions. A corollary of this phenomenon is that larger molecules are produced, for example, pentane, i.e., isopentane and pentane.

Further, rank of coal affects the distillate makeup, the higher the rank of coal, the higher the proportion of liquid distillates under equivalent conditions, e.g., when using the theoretical $K_2S_3$ compound at the same temperature conditions.

Of course, as mentioned before, when the temperature is varied, the product composition changes. Moreover, as illustrated above, when the amount of sulfur in the reagent is changed, the product composition is also changed.

Thus, based on the above, one can vary temperature, sulfur content, rank of coal, and use a recycle of alcohol absorbed distillates (as further explained herein) to obtain the desired product cut. Within variation of a product cut, recycle is contemplated of various other distillates in the recovery train shown in the FIG. 1 herein.

The above described variations are within the following limits: temperature up to 425° C. but distillation starts at 40° to 50° C.; sulfur content in reagent (e.g., for potassium) $K_2S$ but the sulfur content may go up to $K_2S_5$; rank of coal is desirably in the lignite to bituminous coal range. When applied to anthracite, the results are less advantageous although a distillate may be obtained at +380° C. and using a reagent such as $K_2S_4$.

For sodium, the useful sulfur species are NaHS, and the $Na_2S$ to $Na_2S_2$ sulfides; NaHS is more stable than KHS with respect to water in coal or steam and starts reacting to produce a distillate at temperatures correspondingly lower (about 10° to 20° C. lower) from that of potassium, although in somewhat lesser amounts than potassium. Rubidium, while not price advantageous, is at least as good and often even better than potassium.

If the alcoholic distillate (including any hydrocarbon components present) is recycled from separator 14 depicted to the Figure herein to the reaction vessel 11, the product composition may also be varied. Moreover, the amount of recycle may also be varied. Thus, up to about 280° C., the product composition can be forced towards a composition which is a liquid distillate of a boiling point below about 180° C. At a reaction temperature up to about 310° paraffin distillates are formed when employing the above-described alcohol recycle to the reaction vessel. As before, and in this recycle condition, water, i.e., steam at a temperature of about 135° C. and higher must be present in order for the reaction to occur.

For the alcohol recycle, methanol is the preferred alkanol. As can be seen from this aspect of the recycling the alcoholic distillate provides for a further product modification employing the alcohol dissolved initial reaction products in the reaction vessel. As a result of this aspect, more liquid distillates may be obtained.

When starting the process of about ambient conditions (and raising the temperature), elemental sulfur is added to coal or to the reagent to obtain the selected sulfur content for the reagent. At these conditions $H_2S$ formed in the system during the reaction of the sulfur and the reagent is removed from the gas stream and wash system to reconstitute the reagent. As the temperature is being brought up, steam is not used, any hydrogenation of coal that occurs is from the water content in coal or the reagent. At about 135° C., steam may be added if light distillates are desired. Typically, steam is added, however at about the temperature when a hydrate of the reagent starts reforming or reconstitutes itself to a lower hydrate thereof. For potassium based reagent, steam addition temperature is selected at about 170° C.

As the precursor hydrates rearrange to lower hydrates and give up water of hydration, copious amounts of steam are liberated. Thus, that condition signals the point at which steam may be safely introduced, provided the water of hydration has left the reaction vessel.

The process can also be carried out continuously. Generally, a particular temperature level is selected and coal and reagent is introduced in the reaction zone, ashes withdrawn and the reagent and alkali metal part of the reagent recovered therefrom and the reagent reconstituted, e.g., with hydrogen sulfide. The liquid and gaseous fractions are recovered typically in a distillation column or appropriate scrubbers including the hydrogen sulfide. Consequently, a fully continuous process with a reagent reconstitution - recycle is possible based on the illustrations shown herein producing a desired cut of product for the preselected temperature and other operating conditions.

In outlining the complex stages by which the reactions are believed to proceed, it must be remembered that the present understanding is derived by inference as many reactions are simultaneously taking place. Hence, the following explanation is only offered in aid of understanding and not in any way to espouse the correctness of a particular reaction or a theory because this invention can be understood and practiced without reference to any theory.

If it were true that $K_2S_5$ reacts with oxygen in coal, at elevated temperatures, in a closed system, free of atmospheric oxygen, to form $K_2SO_4$ directly, by the displacement of all the coordinated sulfur of the pentasulfide ion by the oxygen, then the reaction would stop when $K_2SO_5$ has been converted to $K_2S_5$.

Thus, $K_2SO_4$ would be inert in the system unless it were converted to carbon monoxide and $K_2S$, by reaction with carbon in coal. If, in fact, this were to happen, then a danger would exist by the reaction of the potassium sulfides with the carbon monoxide to form potassium carbonyl—a highly explosive compound. However, in accordance with the present process, it is fairly clear that the analyzed gases, in the chromatography conduits do not contain appreciable carbon monoxide or carbon dioxide.

It is also known that sulfur, in elemental form, will dehydrogenate coal at temperatures in excess of 175° C. (Mazumdar et al., Fuel, Volume 41, pp. 121 et seq., (1962). Further, air oxidation of potassium pentasulfide produces elemental sulfur, potassium thiosulfate ($K_2S_2O_3$) and potassium tetrathionate ($K_2S_4O_6$). (Letoffe et al., Journal Chimie Physique, Vol. 71, pp. 427-430 (1974). Potassium pentasulfide decomposes into potassium tetrasulfide and sulfur at 300° C.—this reaction is a slow reaction which progressively increases as the temperature is elevated above 300° C.

Potassium sulfide will hold 5 molecules of water of hydration up to 150° C. when it becomes the dihydrate; and the dihydrate is decomposed, at 270° C., to a solid lower hydrate and water and a still lower hydrate to 779° C. to 840° C. at which temperature potassium sulfide decomposes to the disulfide and elemental potassium. Elemental potassium is soluble in the solid sulfide. The thiosulfate ($K_2S_2O_3$) is decomposed above 200° C. to the sulfate plus the pentasulfide and the pentasulfide is, in turn, decomposed to the tetrasulfide and sulfur at temperatures beginning at 300° C.

When the potassium hydrosulfide (in alkanol) is used as the reagent, the water content of the coal and the water present in the solution of the potassium hydrosulfide react to cause hydrolysis and then decomposition to hydrogen sulfide and potassium hydroxide. Potassium hydroxide will react with non-decomposed potassium hydrosulfide to form potassium sulfide (in hydrated form) and water. Potassium pentasulfide (formed by the reaction with the organic sulfur of the coal and the added elemental sulfur) form potassium hydrosulfide as follows:

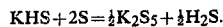

For sodium the reaction is:

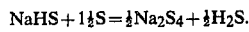

No intermediate sulfur content polysulfides (defined as sulfides with 2 to 5 sulfur atoms) are formed in the reaction with potassium and insufficiency of sulfur will leave unreacted KHS. However, this reaction only occurs in alkaholic solutions. For sodium species only the tetrasulfide species is formed.

Potassium sulfides with a sulfur content less than that of the pentasulfide are decomposed by oxygen to potassium.

In summary, as oxygen is removed as well as nitrogen and organic sulfur, water or hydrogen sulfide (continually produced by contact between water and the reagents) yield hydrogen to the coal at the point where coal has been deoxygenated, desulfurized, or denitrogenated; nitrogen comes off principally as ammonia; the sulfur comes off to form an alkali (e.g. potassium) polysulfide and at lower temperatures forms a mercaptan with the alkanol solvent. Mercaptans are absorbed in alcohol and in the KOH-alcohol solution.

The KOH in the methanol wash for the effluent gas stream gives the alkanol insoluble thiosulfate. This overall reaction proceeds through reduction of the hydrogen sulfide gas to sulfur and water, with subsequent reaction of the sulfur with the KOH to form the potassium thiosulfate and the potassium sulfide as shown above. The potassium sulfide can then acquire additional sulfur from hydrogen sulfide to form potassium polysulfide and are the reagents used in the reaction.

In general, at different temperature levels, the coal breakdown products have different compositional makeup. These temperature levels can be selected for the desired compositional makeup for the volatile distillates and gaseous fractions suitable for a particular end use. For example, at a temperature between 340° C. and 365° C. the following gas analysis was obtained for a product gas obtained from a sub-bituminous coal: methane 80.19%; ethane 9.12%; ethene 1.41%; propane 2.67%; propene 1.41%; iso-butane 0.16%; n-butane 0.31%; hydrogen sulfide 0.001%; and carbonyl sulfide 4.72%; residue unidentified gas components.

From the above, it is demonstrated that a readily available source of hydrocarbons may be realized from coal by a process carried out at low temperature, low pressure while reconstituting the reagent, as part of the process.

What is claimed is:

1. A process for conversion of coal to gaseous hydrocarbons and volatile distillates comprising the steps of:
reacting coal or peat and a hydrosulfide or sulfide of an alkali metal or mixtures thereof in presence of water, up to an amount such that up to a hydrogenated end product of one or two carbon atoms is formed at a temperature between 50° C. and up to 450° C. substantially at atmospheric pressure, and recovering volatile liquid distillates and hydrocarbon gases.

2. In a process as defined in claim 1, further defining said process by the presence of sulfur.

3. A process for conversion of coal to gaseous hydrocarbons and volatile distillates comprising the steps of:
reacting coal and an alkanolic solution of an alkali metal hydrosulfide, a sulfide, a polysulfide or mixtures thereof, or hydrates thereof, at a temperature of 50° C. and above, in the presence of water, up to an amount such that up to a hydrogenated end product of one or two carbon atoms is formed, continuing said reaction at a temperature up to 450° C. and recovering volatile liquid distillates and hydrocarbon gases.

4. The process as defined in claim 3 wherein elemental sulfur is added to said alkanolic solution of said alkali metal hydrosulfide.

5. The process as defined in claim 3 wherein said alkali metal hydrosulfide is potassium hydrosulfide.

6. The process as defined in claim 3 wherein said alkali metal hydrosulfide is sodium hydrosulfide.

7. The process as defined in claim 3 wherein said alkali metal hydrosulfide is a mixture of rubidium, potassium, and sodium hydrosulfides and sulfides.

8. A process for conversion of coal to gaseous hydrocarbons and volatile distillates comprising the steps:
reacting coal or peat having oxygen, sulfur or nitrogen present in bound form with an alkali metal hydrosulfide or polysulfide or mixtures of same or mixed alkali metals thereof, or hydrates thereof, as a reagent;
said reaction being conducted between the temperatures of 135° C. to 450° C. in presence of steam up to an amount such that up to a hydrogenated end product of one or two carbon atoms is formed, said steam being substantially at atmospheric pressure, and without hydrogen being introduced during reaction;
recovering volatile distillates or gaseous hydrocarbons; and
reconstituting said reagent.

9. The process as defined in claim 8 wherein the coal is lignite coal.

10. The process as defined in claim 8 wherein the coal is sub-lignite.

11. The process as defined in claim 8 wherein the coal is bituminous or sub-bituminous coal.

12. The process as defined in claim 8 wherein peat is reacted.

13. The process as defined in claim 8 wherein the alkali metal is potassium.

14. The process as defined in claim 8 wherein the hydrosulfide, sulfide, or polysulfide is of an alkali metal mixture of rubidum, potassium, and sodium.

15. The process as defined in claim 8 wherein the alkali metal is sodium.

16. The process as defined in claim 8 wherein part of 109 distillate is returned as an alcoholic solution to take part in the reaction of coal or peat and said reagent.

17. The process as defined in claim 8 wherein the reaction is conducted at a temperature between 135° C. and 450° C.

18. The process as defined in claim 16 wherein the reaction is conducted at a temperature between 170° C. and 380° C.

19. A continuous process for conversion of coal to gaseous hydrocarbons and volatile distillates comprising the steps of:
introducing continuously into a reaction zone maintained above 50° C. and up to 450° C. coal or peat steamed at a temperature of 100° C. and above at the steam temperature thereof so as to expel air from said coal or peat;
introducing continuously, as a reagent, a hydrosulfide, a sulfide or polysulfide of an alkali metal, or mixed alkali metals and mixtures of hydrosulfides, sulfides and polysulfides thereof or hydrates thereof or said reagent in an alcoholic solution;
introducing water or steam in said reaction zone at a temperature between 50° C. and up to 450° C., up to an amount such that up to a hydrogenated end product of one or two carbon atoms is being formed;
reacting continuously said coal or peat and said reagent in said zone at a predetermined temperature up to 450° C. in the presence of said introduced water or steam substantially at atmospheric pressure;
recovering volatile distillates and/or gaseous products from said reaction zone;
recovering hydrogen sulfide or carbonyl sulfide from said reaction zone;
recovering coal or peat ash from said reaction zone;
recovering unreacted reagent in said coal or peat ash and alkali metal values as alkali metal hydroxide from said coal or peat ash;
reacting alkali metal hydroxides with hydrogen sulfide given off during said reaction and reconstituting said reagent and
introducing a sufficient amount of said reconstituted reagent in said reaction zone so as to continue said reaction of coal or peat and said reagent.

20. The process as defined in claim 19 wherein the reaction zone is maintained at a set, predetermined temperature for production of gaseous hydrocarbons.

21. The process as defined in claim 19 wherein the reaction zone is maintained at a temperature suitable for recovery of a predetermined hydrocarbon cut.

22. The process as defined in claim 19 wherein an alcohol solution containing a portion of said dissolved distillate is recycled to said reaction zone.

23. The process as defined in claim 19 wherein lignite coal is the coal being reacted.

24. The process as defined in claim 19 wherein potassium sulfide, potassium polysulfide, potassium hydrosulfide or a mixture of same is used as a reagent.

25. The process as defined in claim 19 wherein the temperature in said reaction zone is between 135° C. to 450° C.

26. The process as defined in claim 19 wherein the temperature in said reaction zone is between 170° C. and 450° C.

27. The process as defined in claim 19 wherein sodium and potassium hydrosulfide, a sulfide, a polysulfide or a mixture thereof is the reagent.

28. The process as defined in claim 19 wherein a mixture of rubidium, potassium, and sodium polysulfides, sulfides, hydrosulfides, hydrates of the same, or mixtures thereof is used as the reagent.

29. The process as defined in claim 19 wherein industrial sodium hydrosulfide is the reagent.

30. The process as defined in claim 19 wherein the reagent is reconstituted by reacting an alkali metal hydroxide in a saturated alcoholic solution with hydrogen sulfide, precipitating said reagent as a mixture of a sulfide and hydrosulfide of said alkali metal and recovering said precipitate as a reagent for reacting the same with said coal.

31. The process as defined in claim 19 wherein the gaeous hydrocarbon is scrubbed in an alkali metal hydroxide solution thereby removing hydrogen sulfide from said gaseous hydrocarbon as a reaction product with said alkali metal and further recovering said reagent for recycle of same.

32. The process as defined in claim 19 wherein said gaseous hydrocarbon products are distilled for recovery of a desired product cut.

33. The process as defined in claim 19 wherein, as said reagent is used a theoretical composition $K_2S_3$, on basis of material balance.

34. The process as defined in claim 19 wherein anthracite coal is partially reacted with said reagent.

* * * * *